United States Patent [19]
Yamaguchi et al.

[11] Patent Number: 5,972,357
[45] Date of Patent: Oct. 26, 1999

[54] HEALTHY FOODS AND COSMETICS

[75] Inventors: Fumio Yamaguchi; Makoto Saito; Hiroharu Ishikawa; Shigehiro Kataoka; Toshiaki Ariga, all of Noda, Japan

[73] Assignee: Kikkoman Corporation, Japan

[21] Appl. No.: 08/975,713

[22] Filed: Nov. 21, 1997

[30] Foreign Application Priority Data

Dec. 19, 1996 [JP] Japan ................................. 8-353869
Jul. 10, 1997 [JP] Japan ................................. 9-199119
Jul. 10, 1997 [JP] Japan ................................. 9-199120

[51] Int. Cl.$^6$ ........................................ A61K 7/00
[52] U.S. Cl. ..................... 424/401; 514/675; 514/678; 514/690; 514/724; 514/729; 514/730
[58] Field of Search ..................... 426/321, 541, 426/654, 655; 424/401; 514/675, 678, 690, 724, 729, 730

[56] References Cited

FOREIGN PATENT DOCUMENTS

| 249908 | 10/1987 | Japan . |
| 249909 | 10/1987 | Japan . |
| 56614 | 3/1989 | Japan . |
| 83059 | 3/1989 | Japan . |
| 240725 | 10/1991 | Japan . |
| 4-368320 | 12/1992 | Japan . |

OTHER PUBLICATIONS

Krishnamurthy et al., A process for the extraction of gacirnol, hydroxycitric acid and antocyanins which are useful in the food industry as coloring additives from the plant kokum (*Garcinia indica*)., 1998.

Rahbar, "An Abnormal Hemoglobin in Red Cells of Diabetics," Clin. Chem. Acta, vol. 22, 298–300, 1968.

Morimitsu, et al., Protein Glycation Inhibitors From Tyme (*Thymus Vulgaris*), Biosci. Biotech. Biochem., vol. 59, No. 11, 2018–2021, 1985.

Ito, et al., "A Short–Term In Vito Assay For Promotor Substances Using Human Lymphoblastoid Cells Latently Infected With Epstein–Barr Virus," Cancer Letters, vol. 13, 29–37, 1981.

Rao, et al., "Camboginol and Cambogin," Tetra. Lett., vol. 21, 1975–1978, 1980.

Krishnamurthy, et al., "On The Structures of Garcinol, Isogarcinol and Camboginol," Tett. Lett., vol. 22, 793–796, 1981.

*Primary Examiner*—S. Mark Clardy
*Assistant Examiner*—Michael A. Williamson
*Attorney, Agent, or Firm*—Banner & Witcoff, Ltd.

[57] ABSTRACT

The present invention relates to healthy foods and cosmetics. More particularly, it relates to healthy foods and cosmetics containing a polyisoprenylated benzophenone derivatives as effective ingredients and having a variety of functions for maintaining health such as anti-ulcer activity, the Maillard reaction inhibiting activity, anti-oxidation activity, reactive oxygen species scavenging activity, and anti-tumor promotion activity.

5 Claims, No Drawings

HEALTHY FOODS AND COSMETICS

BACKGROUND OF THE INVENTION

1. Field of the Invention

The present invention relates to healthy foods and cosmetics. More particularly, it relates to healthy foods and cosmetics containing a polyisoprenylated benzophenone derivative as an effective ingredient and having a variety of functions for maintaining health such as anti-ulcer activity, the Maillard reaction inhibiting activity, anti-oxidation activity, active oxygen scavenging activity, and anti-tumor promoting activity.

2. Description of Related Prior Art

There have hitherto been used synthetic anti-oxidants such as BHA (tert-butylhydroxyanisole) and BHT (butylhydroxytoluene), and natural anti-oxidants such as vitamin E and vitamin C for the purpose of enhancing the storage stability of high fat foods.

In recent years, among substances having anti-oxidizing activity, those having an activity of scavenging reactive oxygen species or radicals, or an activity of inhibiting the generation of reactive oxygen species in the presence of a metal ion (Fenton reaction) has attracted attention, because reactive oxygen species or radicals are responsible for a variety of diseases as well as the aging of skin such as hardening, development of wrinkles and pigmentation, and the generation of reactive oxygen species in the presence of metal ion causes the oxidative disorders in the body which are responsible for a variety of diseases and the aging of skin described above.

Thus, vitamin E and vitamin C which have hitherto been used as natural antioxidants harmless to the body have been attempted to be used as active oxygen scavenging agents in the body. These materials, notwithstanding their strong anti-oxidizing activities, are not sufficient in relation to their activities for scavenging reactive oxygen species (or radicals) and inhibiting the generation of reactive oxygen species in the presence of metal ion, and thus materials derived from natural substances which have both anti-oxidizing activity and reactive oxygen species scavenging activity such as flavonoids have been searched.

Also, referring to the Maillard reaction, the non-enzymatic browning reaction of proteins with reducing sugars such as glucose has been described by L. C. Maillard, Compt. Rend. Soc. Biol., 72, 599 (1912) and investigated primarily in the field of food science. Since it has been suggested that similar reactions were also observed in the body by S. Rahber, Clin. Chem. Acta, 22, 296 (1968), it has been revealed that the Maillard reaction is intimately responsible for various diseases. Thus, a variety of pharmaceutical agents have been developed on the basis of the anticipation that the inhibition of the Maillard reaction will be effective for the prevention or treatment of these diseases and the aging of skin such as hardening, development of wrinkles and pigmentation.

It has been proposed to use as such agents for example guanidine derivatives such as aminoguanidine, D-penicillamine, quercetin, flavonoids and water soluble carboxyl derivatives of benzophenones, (Japanese Patent Kokai Nos. 249908/1987, 249909/1987, 56614/1989, 83059/1989, 240725/1991 and 368320/1992, and Biosci. Biotech. Biochem., 59, 2018–2021, 1995). These agents have however the defect of less effectiveness.

In addition, referring to the ulcer-preventive effects, protective anti-ulcer agents such as sodium hydrogen carbonate and cetraxate hydrochloride, aggressive anti-ulcer agents such as H2 blockers including cimetidine and ranitidine, proton pump inhibitors such as omeprazole (see Bioindustry, 12(2), 50–58, 1995), and the like are clinically used for the prevention or treatment of peptic ulcers including gastric ulcer and duodenal ulcer. Also, there have still been desired other novel substances effective for these ulcers.

Furthermore, referring to the inhibition of tumor promotion, tumorigenic substances have been classified into two groups in the two-stage process of tumorigenesis proposed in recent years. The two groups comprise the substances which damage DNA and change the normal cells into potential tumor cells (initiator) and the substances which develop the potential tumor cells into tumor (promoter). The typical examples of the former include polycyclic aromatic hydrocarbons, and the typical examples of the latter include phorbol esters. These tumorigenic substances such as the initiator and the promoter are contained in food and drink, air, and the like, and are difficult to remove them completely.

Thus, a method for reducing the risk of tumorigenesis has attracted attention which comprises chemically inhibiting the effects of either one or both of the two stages (see "Chemoprevention of Cancer", Lee W. Wattenberg, Cancer Research, 45, 1–8, 1985). Particularly, the inhibition of the promotion process is very effective for adults, since they are believed to have potential tumor cells which have already been initiated.

For evaluating the effect of anti-tumor promotion, a short-term in vitro method for testing the inhibition of the induction of the Epstein-Barr virus early antigen (EBV-EA) induced by a phorbol ester as a tumor promotor has been developed (see Y. Ito, S. Yanase, J. Fujita, T. Harayama, M. Takashima and H. Imanaka, Cancer Letters, 13, 29–37, 1981).

From the viewpoint described above, substances having the EBV-EA induction inhibiting activities are currently searched particularly with components ingestible everyday. Particularly, substances which have a strong EBV-EA induction inhibiting activity and can be easily produced and processed in an industrial scale are desired. However, no substances have hitherto been found which well satisfy such requirements.

SUMMARY OF THE INVENTION

The object of the present invention is to provide healthy foods and cosmetics which have the Maillard reaction inhibiting activities, anti-oxidation activities, reactive oxygen species (or radicals) scavenging activities, anti-tumor activities and carcinogenesis promotion inhibiting activities and are expected to have prophylactic effects on various geriatric diseases, stress diseases, diabetic diseases, tumorigenesis and the aging of skin such as hardening, wrinkling and pigmentation which are probably caused by the oxidative reaction in the body or the reactive oxygen species.

The present inventors have conducted researches in order to solve the aforementioned problems. As a result, they have found that the extract of the fruit of a plant belonging to Guttiferae (Hyperiaceae) family exhibits the Maillard reaction inhibiting activity, anti-oxidation activity, and a potent reactive oxygen species scavenging activity, and that the purified product of the extract has a strong anti-ulcer activity in the evaluation of ulcer model with rats, and a strong EBV-EA induction inhibiting activity in the EBV-EA induction inhibiting test.

In addition, the present inventors have found that the substance exhibiting the various activities described above is a polyisoprenylated benzophenone derivatives, that the derivatives are contained at a high concentration in the fruit of the above described plant, and that foods or cosmetics having the derivatives incorporated therein are useful as healthy foods and cosmetics.

The present invention is now described in detail below.

DETAILED DESCRIPTION OF THE INVENTION

The polyisoprenylated benzophenone derivative is a derivative in which part or all of the hydrogen atoms on the benzene ring other than the one replaced with a polyisoprenyl group are replaced with hydroxyl groups or carbonyl groups, and may be either water-soluble or oil-soluble. It may be prepared by any methods such as the chemical synthetic method or the extraction of the polyesoprenylated benzophenone derivatives from the plant containing them. In the present invention, either one of the extract or its purified or partially purified product may be used.

The preferred derivatives includes for example well-known substances such as garcinol also known as camboginol, isogarcinol also known as cambogin, xanthochymol, and guttiferone. The particularly preferred one includes garcinol and isogarcinol.

The oil-soluble ones are expected particularly to have a convenience in preparations and a good absorption efficiency into the body.

The plants containing the polyisoprenylated benzophenone derivatives described above are some kind of tropical plants belonging to Guttiferae family, for example *Garcinia cambogia* (English name: Goraka), *Garcinia indica* (English name: Kokam), and *Garcinia purpurea*. Either one of the fruit, pericarp, tree, bark or sap of the plants can be available. The dry fruits of *Garcinia cambogia* and *Garcinia indica* are currently produced in large amounts as acidulants for cooking in various parts of India, and thus these may be available. In recent years, hydroxycitric acid is extracted from the dry fruits described above in a large industrial scale, and thus the extraction residue as the industrial waste produced in the extraction can also be available.

These derivatives can be obtained by the synthetic method, which requires a complicated procedure and thus it is desirable to extract the derivatives from the various plants described above with a conventional technique for example with an organic solvent or a supercritical gas. During the extraction, it is preferred to use an organic solvent since the preferred substance may be extracted in a good efficiency. The organic solvent includes for example (hydrous) methanol, ethanol, acetone and ethyl acetate as well as chloroform, dichloromethane, pentane, hexane, and heptane. Among these solvents, methanol, ethanol and hexane are preferred.

Also, for the extraction with a supercritical gas, carbon dioxide gas is used as the supercritical gas, to which ethanol or water is added as an entrainer, and the extraction can be carried out in an appropriate combination of the conditions of the the temperature of 0–100° C., preferably 20–40° C., and the pressure of 5–2,000 kg/cm$^2$, preferably 20–800 kg/cm , for 5 minutes–4 days, preferably 30 minutes–20 hours.

As described above, any one of the extracts obtained with the organic solvents or the supercritical gas can be used as the healthy foods or cosmetics according to the present invention.

In order to obtain the extract with the above described organic solvent, it is suffice to conduct the extraction according to the well-known method. For example, the fruit, rind, tree, or bark of the plants described above is crushed appropriately, and the crushed product or the sap of the plant is treated with the said organic solvent by the well-known method. Specifically, the raw material is extracted with the organic solvent in an amount of 1–100 times (by weight), preferably 3–20 times (by weight) to that of the raw material, at a temperature of 0° C. or more, preferably at a temperature in the range from 10° C. to the boiling temperature of the organic solvent for 1 minute–8 weeks, preferably 10 minutes–1 week.

While the extraction product thus obtained may be directly used for the healthy foods or cosmetics of the present invention, the organic solvent is more preferably be removed by the conventional method, for example by a rotary evaporator. Furthermore, the product having the organic solvent removed therefrom may be subjected to the conventional treatments such as lyophilization and drying with heating.

In order to purify the polyisoprenylated benzophenone derivatives from the extract, the well-known methods for separating and purifying the natural organic compounds may be employed. By way of example, impurities are removed and purified by such a technique as adsorption or desorption, chromatography, liquid-liquid extraction, or fractional precipitation using active carbon, silica, polymeric carrier etc. Specifically, the extract described above is subjected to ODS-column chromatography and eluted and fractionated with a 60–100% (v/v) ethanol solution (or with a methanol or acetonitrile solution having an appropriate concentration). The components isolated by such chromatographical treatments are collected, concentrated and crystallized to give the polyisoprenylated benzophenone derivative.

In this connection, the derivative thus obtained may be further synthesized into another derivative, which can be also used effectively in the present invention.

The polyisoprenylated benzophenone derivative as the active component of the present invention has a variety of activities useful for maintaining health as described below. That is to say, the derivative has been recognized to have a strong Maillard reaction inhibiting activity in the evaluation thereof by the method described by Hunt et al. below. Additionally, it has been also recognized in the evaluation of the anti-oxidation activity and radical scavenging activity in a water system (emulsion system) as a model described below that the derivative has a strong anti-oxidation activity particularly in the presence of a metal ion, as well as a strong radical scavenging activity, a reactive oxygen species scavenging activity, and a reactive oxygen species generation inhibiting activity. It has been also recognized that the derivative has a strong prophylactic effect in the anti-ulcer test against gastric ulcer and in the anti-ulcer test against stress ulcer induced in rats with an inducing agent described below. In addition, the derivative has been recognized to have a strong tumor promotion inhibiting activity in the EBV-EA induction inhibiting test below. Furthermore, it has been revealed that the derivative has no problem in a toxicity test of a single administration.

Thus, any of the extract, the partially or finally purified product thereof in the purification process can be incorporated in foods and cosmetics to produce the healthy foods and cosmetics of the present invention having many functions required for maintaining health. It goes without say that one or more of the polyisoprenylated benzophenone derivatives can be used in combination. The derivatives having appropriate excipients such as lactose, starch, and fats and oils which are usually used in the art mixed therewith according to necessities are also included in the foods and cosmetics of the present invention.

The ingestive amount of the healthy foods of the present invention is generally in the range of 1–5,000 mg, preferably 20–1,000 mg of the polyisoprenylated benzophenone derivatives per adult person per day. The healthy foods of the present invention is incorporated as a food material into foods and beverages for example in an amount of 0.00001–10% (w/w), preferably 0.0001–5% (w/w) based on the derivative described above.

In the case of utilizing the polyisoprenylated benzophenone derivatives described above as a healthy food material, it may be contained together with a sweetening agent such as sugar and an acidulant such as citric acid and lactic acid when used as a healthy drink, and for example with proteins, sugars, lipids, polyunsaturated fatty acids, vitamins and minerals when used as a healthy food so as the derivatives to be in the concentration described above. The material are not specifically limited to and may be in any forms such as tablets, pills, fine particles, powder, granules, capsules, solutions, suspensions and syrups.

In this connection, the polyisoprenylated benzophenone derivatives can be used not only as a healthy food material, but also as a pharmaceutical such as an anti-ulcer agent or a tumor promotion inhibiting agent. In such cases, the derivative may be used as a blend with appropriate pharmaceutical carriers such as a binder including a syrup, gum arabic, gelatin, sorbitol, or polyvinylpyrrolidone, an excipient including lactose, sucrose, white sugar, corn starch, calcium phosphate, sorbitol, or glycine, a lubricant including magnesium stearate, talc, polyethylene glycol, or silica, a disintegrator including potato starch, a wetting agent including sodium laurylsulfate.

Also, the pharmaceuticals may be in the form of solid preparations such as tablets, pills, fine particles, capsules, or granules, or in the form of liquid preparations such as an aqueous solution, a suspension, an emulsion, a syrup, an elixir, or a limonadae, and these pharmaceuticals are prepared by the conventional methods.

The dose of the derivative used as the pharmaceutical depends on the symptoms to be treated, ages, weights of the subjects, and generally in the range of 10–5,000 mg, preferably 20–2,000 mg per day per adult person based on the polyisoprenylated benzophenone derivatives.

The derivatives can be used as a cosmetic as well. In such case, the derivatives may be blended in an amount of typically 0.00001–10% (w/w), preferably 0.001–5% (w/w) with one or more of fats and oils, surfactants, humidifiers (wetting agent or humidity controlling agent), vitamins, hormones, perfumes, and preservatives which are conventionally used. The blend in such cases may be in the form of creams, emulsions, or aqueous solutions. It can be expected that the cosmetic containing the derivatives exhibits the deterioration suppressing effect by preventing the oxidation of fats and oils contained in the cosmetic, and the effects of scavenging radicals or active oxygen in the body. Furthermore, the derivative has the Maillard reaction inhibiting activity, so that the cosmetic can be also expected to have a prophylactic effect against the deteriorations of skin in association with aging such as hardening, wrinkling and pigmentation.

The present invention is now described in detail below with reference to referential examples, experimental examples and working examples without limitation thereto.

EXAMPLES

Referential Example 1
Preparation of garcinol (camboginol)

Hydroxycitric acid was first extracted and removed from the rind of *Garcinia indica* according to the method described by Y. S. Lewis (see Methods in Enzymology, 77, 615). That is to say, 600 ml of water was added to 200 g of the rind, and the mixture was treated in an autoclave at 115° C. for 15 minutes, filtered by suction through a Buchner filter (using TOYO FILTER PAPER NO. 2), and washed with water until the total amount of the filtrate reached 600 ml. Thus, the extraction residue was obtained.

Next, 500 ml of ethanol was added to 50 g (wet weight) of the extraction residue, and extraction was carried out with stirring at room temperature (20° C.) for 3 hours. The residue was removed by filteration, and the liquid extract was concentrated to dryness in a rotary evaporator to give an extract. It was dissolved in 10 ml of methanol, and after removing the insolubles by filtration, subjected to chromatography on a column (i.d. 32 mm×35 cm) having YMC gel ODS-AM120-S50 (YMC Co., Ltd.) charged therein. Among the components eluted with a 90% acetonitrile solution, the two main fractions having an absorption at 365 nm were collected. Acetonitrile was removed by distillation of the latter yellow eluate fractions using a rotary evaporator to give a pale yellow emulsion. The emulsion was extracted with ethyl acetate in an amount of three times by volume, and the organic layer was dried over anhydrous sodium sulfate, and concentrated to dryness using a rotary evaporator. The dry product was dissolved with heating in a small amount of acetonitrile, and cooled to give pale yellow needles. The crystals were washed with a small amount of cold acetonitrile and then dried in a vacuum desiccator to give 150 mg of crystals as a final product.

The crystalline product has a melting point of 120° C., a specific rotation of −135°, UV absorptions at 250 nm and 365 nm, and a molecular weight measured by mass spectrometry of 602. From these data, the substance was identified as garcinol (camboginol), one of the polyisoprenylated benzophenones described by A. V. Rama Rao et al. (see Tetrahedron Lett., 21, 1975–1978, 1980) and N. Krishnamurthy et al. (see Tetrahedron Lett., 22, 793–796, 1981).

Referential Example 2
Preparation of isogarcinol (cambogin)

In the similar manner as described in Referential Example 1, the former colorless eluate fractions obtained by the ODS column chromatography were collected and concentrated to dryness in a rotary evaporator, and the residue was dissolved in ethanol with heating. Mild cooling gave a colorless plate crystals. The crystals were collected by filtration and dried in a vacuum desiccator to give 15 mg of crystals as the final product.

The crystalline product has a melting point of 218° C., a specific rotation of −203°, UV absorptions at 232 nm and 278 nm, and a molecular weight measured by mass spectrometry of 602. From these data, the substance was identified as isogarcinol (cambogin), one of the polyisoprenylated benzophenones described in the references described above.

Experimental Example 1
Evaluation of anti-oxidation activities

The anti-oxidation activities was evaluated according to the method by A. Ben Aziz et al. (see Phytochemistry, 10, 1445, 1971). That is to say, an emulsion of linoleic acid and β-carotene was first prepared with Tween 20 (Sigma) and adjusted to pH 7.0 with 0.1 M trishydroxyaminomethane-hydrochloride. To the emulsion was added 0.0005% of a substance to be tested, and the mixture was reacted at 25° C.

During the reaction, the color degradation of β-carotene in association with the autoxidation of linoleic acid was measured with the passage of time as the decreased value of the optical density at 460 nm with a spectrophotometer.

The substance to be tested was a garcinal preparation obtained in Referential Example 1, and vitamin E and (+)-catechin were used as Comparative Example. The antioxidant activity was measured as a ratio of the decreasing rate of absorbance in the presence of the substance to be tested to the decreasing rate of absorbance in the absence of the antioxidant. That is, the substance is judged to have an antioxidant activity when the ratio is less than 1, and thus it is predicated that the lesser the ratio, the stronger the antioxidant activity.

As a result, it was revealed that garcinol has an antioxidant activity of 0.50. In this connection, the antioxidant activity was 0.10 for vitamin E and 0.18 for (+)-catechin. Thus, garcinol is revealed to have an antioxidant activity.

Experimental Example 2

Evaluation of anti-oxidation activities in a lipid oxidation process promoted by a metal ion The oxidation process of linoleic acid in Experimental Example 1 is promoted by a metal ion. If 5 $\mu$M of copper sulfate is added to the reaction system, the color-degradation rate of β-carotene is promoted by about 30%. When garcinol was added to this system, the ratio of the decreasing rate of absorbance was 0.57. In this connection, it was 0.13 for vitamin E and 0.84 for (+)-catechin. Thus, garcinol is revealed to have a strong antioxidant activity in the lipid oxidation process catalyzed by the metal ion.

Experimental Example 3

Evaluation of radical scavenging activity

The 1,1-diphenyl-2-picrylhydrazyl (DPPH) radical scavenging activity was tested with a garcinol preparation prepared in the similar manner as described in Referential Example 1. That is to say, a $1.0 \times 10^{-4}$ M solution (50% ethanolic) of DPPH was prepared, 0.0002% of a test substance was added, and the decrease of optical density at 528 nm was measured after 1 hour reaction at 25° C. for one hour. In this case, ascorbic acid was used as a standard, the decrease of the absorbance was expressed as 100, and the radical scavenging activity of the test substance was measured as equivalences to ascorbic acid. In this connection, a garcinol preparaion used as the test substance, and vitamin E and (+)-catechin were used as references.

As a result, the radical scavenging activity was 85 for garcinol. In this connection, it was 25 for vitamin E and 73 for (+)-catechin. Thus, it is revealed that garcinol has a strong radical scavenging activity of about three times per unit weight of vitamin E as an oil-soluble antioxidant.

Experimental Example 4

Evaluation of reactive oxygen scavenging activity

The active oxygen scavenging activity was evaluated according to the superoxide scavenging activity test with phenazine methosulfate. That is to say, dihydronicotinamide adenine dinucleotide and phenazine methosulfate were first reacted in a buffer at a physiological hydrogen ion concentration. The absorbance at 560 nm of a formazan pigment produced by the reduction of Nitro Blue Tetrazolium with superoxide was measured. To the reaction system was added garcinol as the test substance or quercetin or (+)-catechin as the reference samples, respectively. The ratio of decreases of absorbance was expressed as superoxide scavenging activity.

As a result, when the final concentration of the test substance was set at 40 $\mu$M, the superoxide scavenging rate by garcinol was 75%. In the while, the superoxide scavenging rates by quercetin and (+)-catechin as the reference samples was 63% and 25%, respectively.

Thus, garcinol is revealed to have a very strong superoxide scavenging activity, and is useful as an active oxygen scavenger.

Experimental Example 5

Evaluation of the activity for suppressing the generation of reactive oxygen species in the presence of metal ion The activity for suppressing the generation of reactive oxygen species in the presence of metal ion was evaluated by measuring the effect for suppressing the oxidation of bovine serum albumin by hydroxyl radical in the Fenton reaction system. That is to say, hydroxyl radical was first produced by divalent copper ion and hydrogen peroxide (Fenton reaction). Bovine serum albumin was oxidized by the hydroxyl radical, and thus carbonyl was produced. The carbonyl was reacted with 2,4-dinitrophenylhydrazine, and determined by measuring the absorbance at 365 nm. To the reaction system was added garcinol as the test substance or quercetin or (+)-catechin as the reference samples, respectively. The ratio of decreases of absorbance was expressed as the activity for suppressing the generation of reactive oxygen species in the presence of metal ion.

As a result, when the final concentration of the test substance was set at 1 mM, the copper ion concentration was set at 10 $\mu$M, the hydrogen peroxide concentration was set at 20 mM, and the bovine serum albumin concentration was set at 4 mg/ml, the ratio for suppressing the oxidation of bovine serum albumin by garcinol was 55%. In the while, quercetin and (+)-catechin as the reference samples promoted oxidation rather extensively.

Thus, garcinol is revealed to have a strong activity for suppressing the generation of reactive oxygen species in the presence of metal ion.

Experimental Example 6

Evaluation of the Maillard reaction inhibiting activity of garcinol

The Maillard reaction inhibiting activity was evaluated mainly in accordance with the method by Hunt et al. (J. V. Hunt, S. P. Wolff, FEBS Lett., 269, 258–260, 1990). A solution containing bovine serum albumin (4 mg/ml), 500 mM D-fructose and 200 mM potassium phosphate buffer (pH 7.4) was aseptically prepared. To the solution was added 0.1 mM of a test substance. The substance insoluble in water was added as an ethanolic solution so as the final concentration of ethanol to be less than 1%. After incubation of these solutions at 37° C. for 5 days, equivalent volume of a cold 10% trichloroacetic acid solution was added to the solution to precipitate proteins. The precipitate was collected by centrifugation, further washed with a cold 5% trichloroacetic acid solution, and dissolved again in a 200 mM potassium phosphate buffer. The solution was diluted appropriately with distilled water, and the fluorescence intensity at 425 nm was measured with an excitation wave length at 350 nm in a fluorescence spectrophotometer (Shimadzu Seisakusho, Ltd.). The inhibition activity was calculated from the following equation.

$$\text{Inhibition activity } (\%) = (Fc-Fs)/(Fc-Fb) \times 100$$

wherein

Fs: fluorescence intensity in the presence of test substance;

Fc: fluorescence intensity in the absence of test substance;

Fb: fluorescence intensity in the absence of fructose.

As a result, the inhibition activity at 0.1 mM garcinol was 97%. Aminoguanidine which is a known Maillard reaction inhibiting agent exhibited no activity at the concentration of 0.1 mM, and the activity was no more than 43% even at the concentration of 1 mM. Similarly, no activity was observed at 0.1 mM D-penicillamine, and the activity remained 27% even at the concentration of 1 mM. Furthermore, 0.1 mM quercetin exhibited 73% of the inhibition activity, which was less than that of garcinol. Thus, garcinol is a Maillard reaction inhibitor having a high activity.

Experimental Example 7

Evaluation of α-crystallin crosslinking polymerization inhibiting activity

The effect of garcinol on bovine lens α-crystallin crosslinking polymerization reaction was evaluated. A garcinol preparation was obtained in the same manner as described in Referential Example 1. The test was carried out primarily according to the method described by Luthra (M. Luthra and D. Balasubramanian, J. Biol. Chem., 268, 18118–18127, 1993). A solution containing bovine lens α-crystallin (1 mg/ml), 500 mM D-fructose and 200 mM potassium phosphate buffer (pH 7.4) was aseptically prepared. To the solution was added 0.1 mM of a test substance and the mixture was reacted at 37° C. for 2 weeks. Precipitation with trichloroacetic acid was carried out in the same manner as in Experimental Example 6, and the precipitate was disolved again in the phosphate buffer and subjected to the SDS-polyacrylamide electrophoresis by the Laemmli's method. The gel after electrophoresis was stained with Coomassie Brilliant Blue, and the protein amounts in bands were determined with a densitometer. The crosslinking polymerization inhibiting activity of the protein was calculated from the following equation.

Protein polymerization inhibiting activity $(\%) = (Ps - Pc)/Pc \times 100$ wherein polymerization degree of protein=band density of polymerized protein/band density of monomer protein;

Ps: polymerization degree of protein in the presence of test substance;

Pc: polymerization degree of protein in the absence of test substance.

As a result, the protein polymerization inhibiting activity was 68% in garcinol. In the while, it was 33% in quercetin as a reference sample and lower than in garcinol.

Experimental Example 8

Evaluation of tumor promotion inhibiting activity

The effect of inhibiting the tumor promotion was evaluated as follows mainly according to the EBV-EA induction inhibiting test described by Y. Ito et al.

The EBV potentially infected human lymphoblasts (Raji) were first prepared in a concentration of $5 \times 10^5$ cell/ml, and cultured in an RPMI-1640 medium to which 3 mM n-butyric acid (inducer) and 50 nM TPA (12-O-tetradecanoylphorbol-13-acetate) (promoter) were added in an atmosphere of 5% carbon dioxide and 95% air under at a temperature of 37° C. for 48 hours. The cells in which EBV-EA had been induced were detected microscopically by indirect immunofluorescence with the serum of a nasopharyngeal carcinoma (NPC) patient. In this system, various concentrations (8 μg/ml, 40 μg/ml, and 200 μg/ml) of the test substance (garcinol sample shown in Referential Example 1) dissolved in DMSO (dimethylsolfoxide) were added together with the promoter to the cells. The activity of suppressing the induction of the Epstein-Barr virus early antigen was defined as the decreasing rate of the cells in which EBV-EA had been induced.

As a result, garcinol suppressed 58.2% of the induction of EBV-EA in the presence of 8 μg/ml of garcinol in the medium, and the survival rate of the cells were 80% or more.

It has been found from these results that garcinol, a polyisoprenylated benzophenone derivative has a strong activity of suppressing the induction of EBV-EA, and the preparation containing garcinol as an effective component can suppress the induction of EBV-EA. The derivative can be utilized as a healthy food or as a pharmaceutical because of such activity.

Experimental Example 9

Anti-ulcer test of the inducing agent against ulcer

Ulcer was induced in Wistar/ST male rats having a weight of about 200 g (6 week-old) by indomethacin as a gastric ulcer inducing agent, and the anti-ulcer effects of the test samples were examined in the following six groups to which test samples were administered.

Each group comprises six rats.

Animal Groups

| Group 1: | (control) physiological saline |
| Group 2: | (comparative) cetraxate hydrochloride 200 mg/kg |
| Group 3: | (the present invention) garcinol 200 mg/kg |
| Group 4: | (the present invention) garcinol 100 mg/kg |
| Group 5: | (the present invention) garcinol 50 mg/kg |
| Group 6: | (the present invention) isogarcinol 200 mg/kg |

In this connection, physiological saline containing 1% sodium carboxymethylcellulose was used as the control, and cetraxate hydrochloride (trade name "Neuer®S", Daiichi Pharmaceuticals Co., Ltd.) which is clinically used as an anti-ulcer agent was used as the comparative sample. The cetraxate hydrochloride insoluble in water was ground into fine powder with a mortar and a pestle and used as a suspension in a 1% sodium carboxymethylcellulose solution. Also, garcinol and isogarcinol in the form of fine powder were used as the suspensions in a 1% sodium carboxymethylcellulose solution in the concentrations which are the doses in the groups. In this connection, garcinol and isogarcinol used in the section of the present invention were those obtained in Referential Examples 1 and 2, respectively.

Experimentals Method and Evaluation

Experiment was carried out according to the method described by Yamahara et al. (see YAKUGAKU ZASSHI, 114, 401, 1994) which had been slightly modified. That is to say, indomethacin (50 mg/kg) was suspended in 1% sodium carboxymethylcellulose containing 0.1% Tween 20 (Sigma) and injected subcutaneously into the back of 24 hour fasted rats in an amount of 1 ml/rat. The samples in the six sections were orally administered at 30 minutes before administration of indomethacin. After 7 hours from the administration of indomethacin, rats were bleeded to death under anesthetization with nembutal, and stomach was isolated. A phosphate buffer (10 ml) containing 10% formalin was injected into the stomach, which was cut open after 10 minutes, and the length of lesion caused in the glandular stomach portion was defined as the lesion index, which was measured in the mm unit to evaluate the anti-ulcer effect. The result is shown in Table 1. The suppression rate (%) in Table 1 means the value in which the difference of the length (mm) of ulcer in each group subtracted from the average length, 47.75 (mm) of ulcer in the control was divided with the average length, 47.75 (mm) of ulcer in the control. The larger the value, the stronger the anti-ulcer activity.

TABLE 1

|  | Length of ulcer (mm) | Suppression rate (%) |
|---|---|---|
| Group 1 (control) | 47.75 ± 6.08 | 0 |
| Group 2 (comparative) | 14.30 ± 10.9 | 70.1 |
| Group 3 (the present invention) | 3.00 ± 5.35** | 93.7 |
| Group 4 (the present invention) | 4.00 ± 4.32** | 91.6 |
| Group 5 (the present invention) | 5.75 ± 6.13** | 88.0 |
| Group 6 (the present invention) | 22.40 ± 15.3* | 53.1 |

Note:
*represents that the group is significant in relation to the group 1 with a level of significance of 5%; and
**represents that the group is significant in relation to the group 1 with a level of significance of 1%.

As is apparent from Table 1, any groups in the present invention has a significantly strong anti-ulcer activity in relation to the control. Particularly, in the groups with 200 mg/kg, 100 mg/kg and 50 mg/kg of garcinol, extremely strong anti-ulcer activities over the group with cetraxate hydrochloride as a commercially available anti-ulcer agent were shown. Thus, the polyisoprenylated benzophenone derivatives are revealed extremely useful as anti-ulcerative healthy foods and as anti-ulcerative pharmaceuticals.

Experimental Example 10

Anti-ulcer test against stress ulcer

Gastric ulcer was induced in Wistar/ST male rats having a weight of about 200 g (6 w) by the stress of restrained immersion into water and the anti-ulcer effects of the test samples were examined in the following groups to which test samples were administered.

Each group comprises six rats.

Animal groups

Group 1: (control) physiological saline

Group 2: (comparative) cetraxate hydrochloride 200 mg/kg

Group 3: (the present invention) garcinol 200 mg/kg

In this connection, the test samples in the control, comparative group and the present invention group were prepared in the same manner as in Experimental Example 9.

Experimental Method and Evaluation

Rats having fasted for 24 hours were locked up in a restrained dipping cage after 30 minutes from the oral administration of respective test samples. Next, rats were stressed by dipping the cage into water at 23° C. for 7 hours, and bleeded to death under anesthetization with nembutal, and stomach was isolated. A phosphate buffer (10 ml) containing 10% formalin was injected into the stomach, which was cut open after 10 minutes, and the length of lesion caused in the glandular stomach portion was defined as the lesion index, which was measured in the mm unit to evaluate the anti-ulcer effect.

The result is shown in Table 2. The method for calculating the suppression rate (%) and the meaning of it has been described in Experimental Example 9.

TABLE 2

|  | Length of ulcer (mm) | Suppression rate (%) |
|---|---|---|
| Group 1 (control) | 44.20 ± 18.10 | 0 |
| Group 2 (comparative) | 18.80 ± 6.02* | 57.5 |
| Group 3 (the present invention) | 17.60 ± 9.96* | 60.2 |

*represents that the group is significant in relation to the control with a level of significance of 5%.

As is apparent from Table 2, the group of the present invention exhibited substantially equivalent anti-ulcer activity to that of the commercially available cetraxate hydrochloride.

Thus, the polyisoprenylated benzophenone derivatives are revealed effective for the prophylaxis or treatment of ulcer induced by stress when used as healthy foods and as pharmaceuticals.

Experimental Example 11

Toxicity test by single administration

Test animal

ICR/crj male mice (5 week-old) having a weight of 29–32 g, each group comprising 5 animals.

Experimental method

Toxicity test by single administration was carried out in accordance with Guidelines of the Toxicity Test Method for Pharmaceuticals (Nichi-Yaku-Shin No. 118, released on Feb. 15, 1984, Notice of Second Section Manager of Examination of Pharmaceutical Affairs Bureau in Ministry of Health and Welfare to the Managers of Hygiene Division of Prefectures).

Garcinol was suspended into a physiological saline in a concentration of 30 mg/ml, and the suspension was administered orally to mice at a dose of 0.5 ml per 30 g of body weight (500 mg/kg of body weight) for observation for 14 days.

As a result, no mortality was observed, no side-effects were recognized, and no microscopic disorders in tissues or organs were observed in the autopsy on 14 days, so that garcinol used in the present invention is revealed to have extremely low toxicity.

Example 1

Healthy drinks with extracts

In the same manner as in Referential Example 1, the hydroxycitric acid extracted residue of the dry rind of Garcinia indica was extracted with ethanol to give an extract (containing 25% w/w of garcinol and 5% w/w of isogarcinol).

The contents of garcinol and isogarcinol in the extract were confirmed by high performance liquid chromatography with use of the crystallized samples prepared in Referential Examples 1 and 2 as the standard samples.

The extract was incorporated to prepare 1 kg of a healthy drink having the following composition.

Composition of the Healthy Drink

| | |
|---|---|
| sucrose | 3.0% |
| syrup of fructose and glucose | 7.0% |
| ethanol | 0.8% |
| *Garcinia indica* extract | 0.3% |
| citric acid | 0.1% |
| water | 88.8% |

90–450 mg of the polyisoprenylated benzophenone derivatives (garcinol and isogarcinol) can be ingested by drinking 100–1,000 g of the healthy drink per day.

Example 2
Healthy food (in the form of fine particles) with extracts

An extract (containing 25% w/w of garcinol, 5% w/w of isogarcinol) obtained in the same manner as in Example 1 was incorporated to prepare 1 kg of a healthy food having the following composition (unit: g).

For the soy protein isolate in the composition, "NEW FUJI PRO 1200" (FUJI PURINA PROTEIN CO., Ltd.) was used.

Composition of the Healthy Food (Per 1 kg)

| | |
|---|---|
| *Garcinia indica* extract | 50.0 |
| soy protein isolate | 904.446 |
| hydrous crystalline glucose | 30.3 |
| dextrin | 3.0 |
| vitamin B1 | 0.05 |
| vitamin B2 | 0.06 |
| vitamin B6 | 0.15 |
| vitamin B12 | 0.00018 |
| folic acid | 0.024 |
| vitamin A | 0.22 |
| ascorbic acid | 2.0 |
| α-dl-tocopherol | 0.75 |
| calcium lactate | 9.0 |

450 mg of the polyisoprenylated benzophenone derivatives (garcinol and isogarcinol) can be ingested by eating 30 g of the healthy food per day.

Example 3
Healthy food in the form of soft capsules with extracts

An extract (containing 25% w/w of garcinol and 5% w/w of isogarcinol) obtained in the same manner as in Example 1 was incorporated to prepare a healthy food in the form of soft capsules which has the following composition (unit: mg).

Composition of the Healthy Food (Per 1 Capsule)

| | |
|---|---|
| *Garcinia indica* extract | 50.0 |
| β-carotene | 20.0 |
| α-dl-tocopherol | 0.75 |
| DHA | 30.0 |
| olive oil | 899.25 |

15–450 mg of the polyisoprenylated venzophenone derivatives (garcinol and isogarcinol) can be ingested by eating 1–30 capsules of the healthy food in the form of soft capsules per day.

Also, the healthy food has an effect for preventing the oxidation of DHA in the composition.

Example 4
skin cosmetics (cream)

A garcinol sample obtained in the same manner as in Referential Example 1 was incorporated to prepare 100 g of a skin cosmetics having the following composition (unit: % w/w) and exhibiting the anti-oxidation activity, the active oxygen scavenging activity and the Maillard reaction inhibiting activity. The cosmetics can be expected to have a prophylactic effect against the deterioration of skin in association with aging such as hardening, wrinkling, and pigmentation.

Composition of cream

| | |
|---|---|
| garcinol | 0.1% |
| liquid paraffin | 10.0% |
| isopropyl palmitate | 5.0% |
| cetanol | 5.0% |
| glyceryl monostearate | 1.5% |
| POE(40) monostearate | 1.5% |
| glycerin | 5.0% |
| perfume | q.s. |
| preservative | q.s. |
| purified water | balance |

Example 5
Anti-ulcer syrup containing garcinol

Garcinol prepared in the same manner as described in Referential Example 1 was pulverized in a mortar, suspended in a sterile purified water, and cherry syrup was added to the suspension with gentle stirring to give 1200 ml of a syrup preparation having the following composition. The syrup is an anti-ulcer agent (syrup) which can be administered 1–3 times a day, and 5 ml of dosage contains 200 mg of garcinol.

Composition of syrup

| | |
|---|---|
| garcinol | 48 g |
| sterile purified water | balance |
| cherry syrup | 1000 ml |
| total | 1200 ml |

Example 6
Anti-ulcer powder containing garcinol

Garcinol prepared in the same manner as described in Referential Example 1, lactose and crystalline cellulose were blended, and kneaded with purified water to give 1 kg of a powder preparation in the form of powder or fine particles by the conventional method.

The powder preparation is an anti-ulcer agent (powder) having a content of 1 g per packet and containing 200 mg of garcinol per dosage of a packet.

Composition of powder

| | |
|---|---|
| garcinol | 200 g |
| lactose | 600 g |
| crystalline cellulose | 200 g |

Example 7
Anti-ulcer powder containing isogarcinol

Isogarcinol prepared in the same manner as described in Referential Example 2, lactose and crystalline cellulose were blended, and kneaded with purified water to give 1 kg of a powder preparation in the form of powder or fine particles by the conventional method.

The powder preparation is an anti-ulcer agent (powder) having a content of 1 g per packet and containing 200 mg of isogarcinol per dosage of a packet.

| Composition of powder | |
|---|---|
| isogarcinol | 200 g |
| lactose | 600 g |
| crystalline cellulose | 200 g |

The healthy foods and cosmetics of the present invention comprising the polyisoprenylated benzophenone derivatives have strong anti-oxidation activities, particularly strong anti-oxidation activities in the presence of metal ion, and strong radical scavenging activity. Furthermore, the healthy foods and cosmetics of the present invention have strong active oxygen (superoxide) scavenging activities and activities for suppressing the generation of reactive oxygen species (hydroxyl radical) in the presence of metal ion, so that the effects for preventing or reducing various disorders in the body in which the reactive oxygen species are believed to participate can be expected. Also, the healthy foods or cosmetics of the present invention have strong Maillard reaction inhibiting activities, so that effects for preventing or treating the disease (diabetic complication) and the prophylactic effects against the deterioration of skin involved in aging such as hardening, wrinkling and pigmentation are also expected. Furthermore, the healthy foods of the present invention have activities for suppressing the induction of Epstein-Barr virus early antigen, so that the foods is expected to have the carcinogenesis preventing effect. In addition, the healthy foods of the present invention also have strong anti-ulcer activities, and are effective for the prophylaxis or treatment of peptic ulcer, particularly for the prophylaxis or treatment of gastric ulcer. And the effective components of the healthy foods or cosmetics of the present invention has extremely low toxicity.

Thus, the polyisoprenylated benzophenone derivatives as the effective components of the present invention have various functions intimately relating to the maintenance of health, so that these derivatives can be used as foods and drinks, healthy foods, food additives or cosmetics as well as pharmaceuticals are extremely useful in industry.

What is claimed is:

1. A cosmetic comprising a polyisoprenylated benzophenone derivative.

2. The cosmetic of claim 1 wherein said polyisoprenylated benzophenone derivative is present in an amount from 0.00001% to 10% by weight.

3. The cosmetic of claim 1 wherein said polyisoprenylated benzophenone derivative is present in an amount from 0.001% to 5% by weight.

4. The cosmetic of claim 1 wherein said polyisoprenylated benzophenone derivative is an organic extract of a plant belonging to the Guttiferae (Hyperiaceae) family.

5. The cosmetic of claim 1 wherein said polyisoprenylated benzophenone derivative is a garcinol.

* * * * *